United States Patent
Ditter

(10) Patent No.: US 12,207,931 B2
(45) Date of Patent: *Jan. 28, 2025

(54) CATHETER WITH SOFT DISTAL TIP FOR MAPPING AND ABLATING TUBULAR REGION

(71) Applicant: Biosense Webster (Israel) Ltd., Yokneam (IL)

(72) Inventor: Tom Allen Ditter, Mission Viejo, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 851 days.

This patent is subject to a terminal disclaimer.

(21) Appl. No.: 17/113,976

(22) Filed: Dec. 7, 2020

(65) Prior Publication Data

US 2021/0085205 A1 Mar. 25, 2021

Related U.S. Application Data

(63) Continuation of application No. 16/195,749, filed on Nov. 19, 2018, now Pat. No. 10,856,757, which is a
(Continued)

(51) Int. Cl.
*A61B 5/287* (2021.01)
*A61B 5/00* (2006.01)
(Continued)

(52) U.S. Cl.
CPC ............ *A61B 5/287* (2021.01); *A61B 5/0538* (2013.01); *A61B 5/6857* (2013.01);
(Continued)

(58) Field of Classification Search
CPC .... A61B 2018/1435; A61B 2018/1437; A61B 5/283; A61B 5/293; A61B 5/6856; A61B 5/6857
See application file for complete search history.

(56) References Cited

U.S. PATENT DOCUMENTS

| | | |
|---|---|---|
| 5,820,591 A | 10/1998 | Thompson et al. |
| 5,964,757 A | 10/1999 | Ponzi |
| | (Continued) | |

FOREIGN PATENT DOCUMENTS

| | | |
|---|---|---|
| CN | 102961183 A | 3/2013 |
| EP | 2759276 A1 | 7/2014 |
| | (Continued) | |

OTHER PUBLICATIONS

European Search Report dated Apr. 22, 2016 for European Patent Application No. 15195289.2, 8 pages.
(Continued)

*Primary Examiner* — Eun Hwa Kim
(74) *Attorney, Agent, or Firm* — Frost Brown Todd LLP

(57) ABSTRACT

A catheter includes an elongated body having a longitudinal axis, a distal assembly distal the elongated body, the distal assembly having a tapered helical form comprising a larger, electrode-carrying proximal loop and a smaller, softer distal loop, and a shape-memory support member extending through at least the proximal loop. For example, the helical loop subtends at least about 720 radial degrees, with the proximal loop subtending about 360 radial degrees, and the distal loop subtending about 360 radial degrees. The softer distal loop with a straight distal end atraumatically guides the distal assembly into a tubular region so that the larger proximal loop can sit on the ostium of the tubular region with improved electrode and tissue contact.

20 Claims, 12 Drawing Sheets

Related U.S. Application Data continuation of application No. 15/785,303, filed on Oct. 16, 2017, now Pat. No. 10,130,422, which is a continuation of application No. 14/549,438, filed on Nov. 20, 2014, now Pat. No. 9,788,893.

(51) Int. Cl.
*A61B 5/0538* (2021.01)
*A61B 18/14* (2006.01)
*A61B 17/00* (2006.01)
*A61B 18/00* (2006.01)
*A61B 18/12* (2006.01)
*A61B 34/20* (2016.01)

(52) U.S. Cl.
CPC .............. *A61B 18/1492* (2013.01); *A61B 2017/00867* (2013.01); *A61B 2018/00029* (2013.01); *A61B 2018/00166* (2013.01); *A61B 2018/00375* (2013.01); *A61B 2018/00577* (2013.01); *A61B 2018/00642* (2013.01); *A61B 2018/00702* (2013.01); *A61B 2018/00797* (2013.01); *A61B 2018/00821* (2013.01); *A61B 2018/00839* (2013.01); *A61B 2018/00875* (2013.01); *A61B 2018/0091* (2013.01); *A61B 2018/124* (2013.01); *A61B 2018/1435* (2013.01); *A61B 2018/1467* (2013.01); *A61B 2034/2051* (2016.02); *A61B 2218/002* (2013.01); *A61B 2562/0214* (2013.01)

(56) References Cited

U.S. PATENT DOCUMENTS

| | | | |
|---|---|---|---|
| 6,064,902 A | 5/2000 | Haissaguerre et al. | |
| 6,371,955 B1 | 4/2002 | Fuimaono et al. | |
| 6,468,260 B1 | 10/2002 | Bumbalough et al. | |
| 6,500,167 B1 | 12/2002 | Webster, Jr. | |
| 6,522,933 B2 | 2/2003 | Nguyen | |
| 6,532,378 B2 | 3/2003 | Saksena et al. | |
| 6,745,080 B2 | 6/2004 | Koblish | |
| 6,972,016 B2 | 12/2005 | Hill, III et al. | |
| 7,008,401 B2 | 3/2006 | Thompson et al. | |
| 7,285,119 B2 | 10/2007 | Stewart et al. | |
| 7,771,421 B2 | 8/2010 | Stewart et al. | |
| 7,959,630 B2 | 6/2011 | Taimisto et al. | |
| 8,206,384 B2 | 6/2012 | Falwell et al. | |
| 8,257,351 B2 | 9/2012 | Stewart et al. | |
| 8,475,450 B2 | 7/2013 | Govari et al. | |
| 8,565,851 B2 | 10/2013 | Lau et al. | |
| 8,608,735 B2 | 12/2013 | Govari et al. | |
| 8,639,310 B2 | 1/2014 | Chen et al. | |
| 9,788,893 B2 | 10/2017 | Ditter | |
| 10,130,422 B2 | 11/2018 | Ditter | |
| 2004/0167509 A1 | 8/2004 | Taimisto | |
| 2005/0033135 A1 | 2/2005 | Govari | |
| 2005/0070887 A1 | 3/2005 | Taimisto et al. | |
| 2006/0106295 A1 | 5/2006 | Jais et al. | |
| 2007/0219546 A1 | 9/2007 | Mody et al. | |
| 2011/0054287 A1 | 3/2011 | Schultz | |
| 2011/0054446 A1 | 3/2011 | Schultz | |
| 2011/0160719 A1 | 6/2011 | Govari et al. | |
| 2012/0116200 A1* | 5/2012 | Roy | A61B 5/287 600/374 |
| 2012/0172703 A1 | 7/2012 | Esguerra et al. | |
| 2013/0006238 A1* | 1/2013 | Ditter | A61B 18/1492 606/41 |
| 2013/0304062 A1* | 11/2013 | Chan | A61B 18/1492 606/41 |
| 2014/0148805 A1* | 5/2014 | Stewart | A61B 18/1492 606/41 |
| 2015/0246206 A1* | 9/2015 | Schultz | A61M 25/0136 600/374 |

FOREIGN PATENT DOCUMENTS

| | | |
|---|---|---|
| EP | 1565118 B1 | 9/2016 |
| WO | 9605768 A1 | 2/1996 |
| WO | 2013059511 A1 | 4/2013 |

OTHER PUBLICATIONS

Australian First Office Action dated Jul. 25, 2019, for Application No. 2015261570, 4 pages.
Chinese First Office Action and Search Report dated May 28, 2019, for Application No. 201510809737.2, 7 pages.
Chinese Second Office Action and Search Report dated Mar. 31, 2020, for Application No. 201510809737.2, 9 pages.
Japanese First Office Action dated Oct. 1, 2019, for Application No. 2015-226366, 4 pages.
European Communication dated Nov. 9, 2018, for Application No. 15195289.2, 7 pages.
European Communication dated Aug. 12, 2019, for Application No. 15195289.2, 7 pages.
European Extended Search Report and Written Opinion dated Sep. 5, 2019, for Application No. 19185013.0, 10 pages.
European Communication dated Oct. 11, 2023, for Application No. 19185013.0, 8 pages.

* cited by examiner

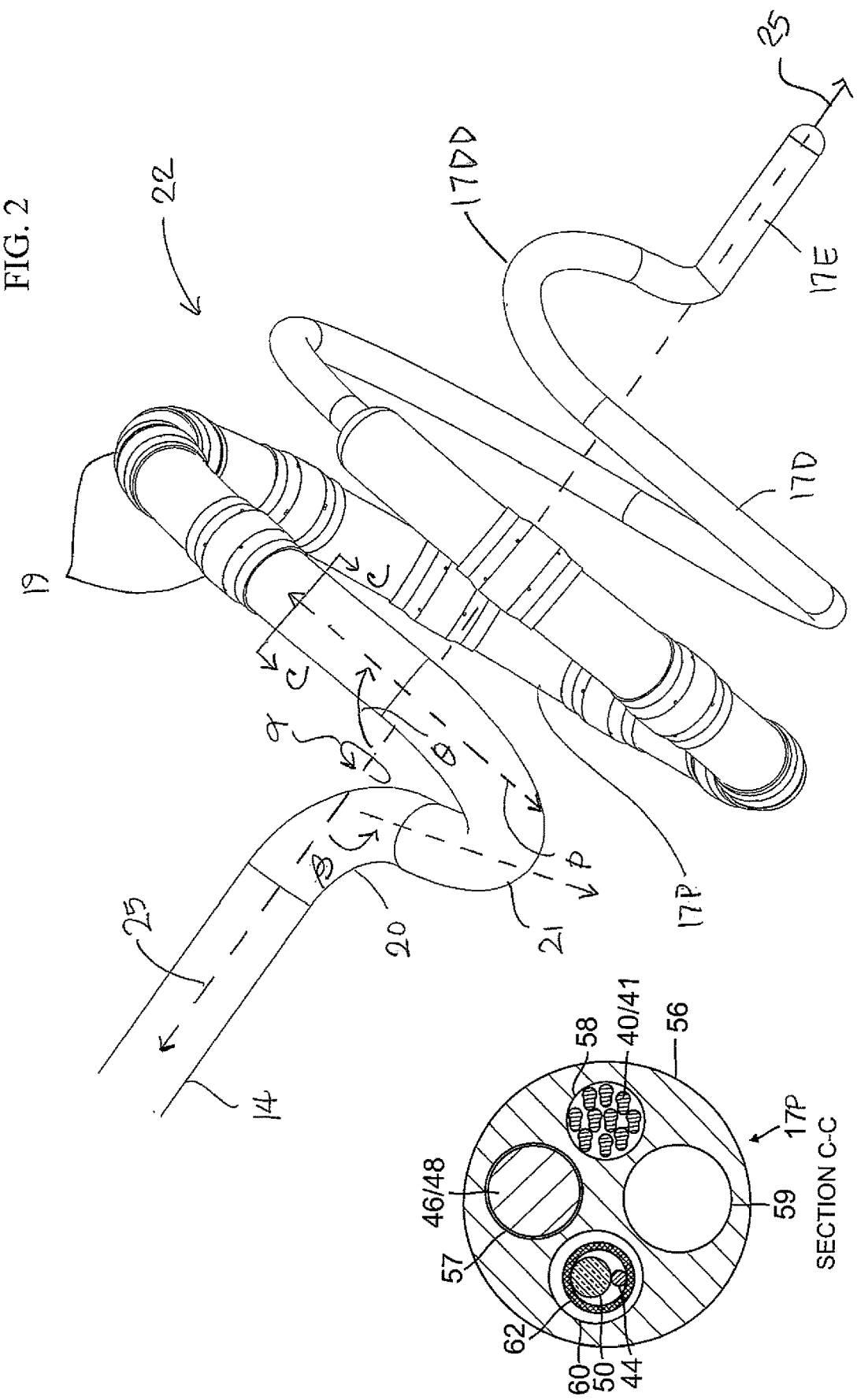
FIG. 2
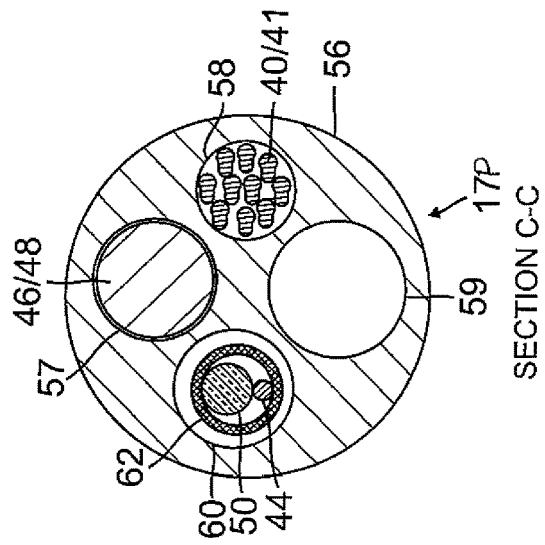
FIG. 2A  SECTION C-C

CATHETER WITH SOFT DISTAL TIP FOR MAPPING AND ABLATING TUBULAR REGION

CROSS-REFERENCE TO RELATED APPLICATION(S)

This application is a continuation of and claims priority to and the benefit of U.S. application Ser. No. 16/195,749 filed Nov. 19, 2018, now U.S. Pat. No. 10,856,757, which is a continuation of and claims priority to and the benefit of U.S. patent application Ser. No. 15/785,303 filed Oct. 16, 2017, now U.S. Pat. No. 10,130,422, which is a continuation of and claims priority to and the benefit of U.S. application Ser. No. 14/549,438 filed Nov. 20, 2014, now U.S. Pat. No. 9,788,893, the entire contents of all of which are incorporated herein by reference.

FIELD OF INVENTION

This invention relates generally to methods and devices for invasive medical treatment, and specifically to catheters, in particular, catheters having distal sections adapted for mapping and ablating selected anatomy.

BACKGROUND

Ablation of myocardial tissue is well known as a treatment for cardiac arrhythmias. In radio-frequency (RF) ablation, for example a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary vein has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Patent Application Publication 2005/0033135, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section is connected to catheter by a generally straight axial base section that is in an "on edge" configuration where the base axial section connects to the curved section on the circumference of the curved section. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. Pat. No. 7,008,401, whose disclosure is incorporated herein by reference, describes compound steering assemblies, usable in both diagnostic and therapeutic applications, for steering the distal section of a catheter in multiple planes or complex curves. These assemblies are said to enable a physician to swiftly and accurately position and maintain ablation and/or mapping electrodes in intimate contact with an interior body surface. U.S. Pat. No. 5,820,591, whose disclosure is incorporated herein by reference, similarly describes compound steering assemblies of this sort.

U.S. Pat. No. 8,608,735, issued on Dec. 17, 2013, whose disclosure is incorporated herein by reference, describes a medical device, including an insertion shaft, having a longitudinal axis and having a distal end adapted for insertion into a body of a patient. A resilient end section is fixed to the distal end of the insertion shaft and is formed so as to define, when unconstrained, an arc oriented obliquely relative to the axis and having a center of curvature on the axis. One or more electrodes are disposed at respective locations along the end section.

However, because human anatomy varies between individuals, the shape and size of an ostium vary, and the end section whether having an arcuate shape or a generally circular shape may not always fit the particular target ostium. Moreover, because the right atrium is a confined volume, the approach into a PV ostium is often times indirect in that the distal section does not always assume a perpendicular angle to the target site. Because of these factors, contact between the electrodes and the ostium is often less than complete. If pressure is applied in the axial direction to the distal section in an attempt to improve electrode contact with the ostium, and/or if the catheter is rotated about its longitudinal axis, the distal section may slip off the ostium.

Accordingly, a desire exists for a lasso-type catheter that can provide a distal section whose curved (or circular, used interchangeably herein) portion can be inserted atraumatically into a tubular region, such as a pulmonary vein, to ensure placement accuracy of the electrodes at the ostium of the pulmonary vein and minimize the risk of the curved portion dislodging from the ostium when increased pressure is applied or the curved portion is rotated about the ostium.

SUMMARY OF THE INVENTION

The present invention is directed to a steerable, multi-electrode, irrigated, luminal catheter that is particularly useful for deployment in the atria of the heart through a guiding sheath. The catheter is configured to facilitate electrophysiological mapping of the atria and to transmit radiofrequency (RF) current to the catheter electrodes for ablation purposes. The catheter includes an arcuate resilient distal assembly, wherein the distal assembly has a tapered helical form including a larger proximal loop and a smaller distal loop adapted for use in a tubular region. Whereas the distal loop has a smaller radius, a softer structure with a greater flexibility, and a softer straight distal end section that helps guide the distal loop into the tubular region, the proximal loop has a stiffer structure and a larger radius to ensure contact between its electrodes and the ostium of the tubular region. The softer straight distal end section provides an atraumatic leading element that guides the distal loop into the tubular region and ensures placement accuracy of the proximal loop, especially when an axial force is applied by the user.

The centered, tapered helical form of the distal assembly allows for improved tissue contact and annular motion. The helical form has a predetermined pitch that provides gentle pressure to ensure contact of the electrodes in the distal assembly with the ostium. The tapered helical form ensures that the distal loop can fit into the tubular region which in turn ensures placement accuracy of the proximal loop and ablation electrodes thereon on the ostium.

The pitch of the helical form can be varied along the length of the helical form. For example, the pitch of the proximal loop can be greater than the pitch of the distal loop. Alternatively, both the pitch and the radius of helical form can be varied along the length of the helical form.

In some embodiments, the catheter includes an elongated body having a longitudinal axis, a distal assembly distal the elongated body, the distal assembly having a helical form comprising a proximal loop and a distal loop, and a shape-memory support member extending through at least the proximal loop. The catheter also includes at least one irrigated ablation ring electrode mounted on the proximal loop, and a control handle proximal the elongated body, wherein the proximal loop has a lesser flexibility and the distal loop has a greater flexibility.

In some detailed embodiments, the helical form subtends at least about 720 radial degrees, with the proximal loop subtending about 360 radial degrees, and the distal loop subtending about 360 radial degrees.

In some detailed embodiments, the helical form is on axis relative to a longitudinal axis of the catheter. A generally straight distal end extends distally from the distal loop which is also on-axis relative to the longitudinal axis.

In some detailed embodiments, the helical form is tapered, wherein the proximal loop has a greater radius and the distal loop has a lesser radius.

In some detailed embodiments, the proximal loop and the distal loop are oriented obliquely at an angle relative to a longitudinal axis of the catheter. In some more detailed embodiments, the oblique angle ranges between about 45 degrees to 105 degrees, preferably between about 75 to 105 degrees, and more preferably the oblique angle is about 90 degrees.

In some embodiments, the proximal loop includes between about eight to twenty electrodes, and preferably about ten electrodes, which subtend about 360 radial degrees. Alternatively, the proximal loop includes about six electrodes which subtend about 180 radial degrees.

In some detailed embodiments, the distal loop includes ring electrodes for sensing electrical potentials.

The catheter may also comprise a contraction wire extending through the elongated body and the distal assembly, wherein the control handle includes a first control member configured to actuate the contraction wire to contract the helical form.

The catheter may also further comprise a deflection wire extending through the elongated body, wherein the control handle includes a second control member configured to actuate the deflection wire to deflect a portion of the elongated body.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2 is a detailed view of a distal assembly of the catheter of FIG. 1.

FIG. 2A is a cross-sectional view of the distal assembly of FIG. 2, taken along line C-C.

DETAILED DESCRIPTION OF THE INVENTION

Lasso catheters, as described above, may be used for mapping and ablating tissue along an arc or curve surrounding an anatomical structure, such as the ostium of a pulmonary vein. The lasso is generally made thin and flexible, for purposes of maneuverability, with large ring electrodes to minimize electrical resistance. U.S. Pat. No. 8,475,450, issued Jul. 2, 2013, entitled DUAL-PURPOSE LASSO CATHETER WITH IRRIGATION, which is assigned to the assignee of the present patent application and whose disclosure is incorporated herein by reference, describes an alternative design in which the lasso is thicker and stiffer. U.S. patent application Ser. No. 13/174,742, filed Jun. 30, 2011 (now published as 2013/0006238), which is assigned to the assignee of the present patent application and whose disclosure is incorporated herein by reference, describes a lasso catheter whose distal assembly has a curved configuration that can be varied by means of a contraction wire actuated by a control handle.

Embodiments of the present invention that are described hereinbelow provide probes, such as catheters, with improved lasso-type structures to facilitate maneuvering and positioning in the heart. Such catheters can be used to produce curved, circular, looped or otherwise closed ablation paths, as well as sensing electrical activity along a curve, circle, loop or closed pattern for electrical potential and anatomical mapping.

Figure 1:
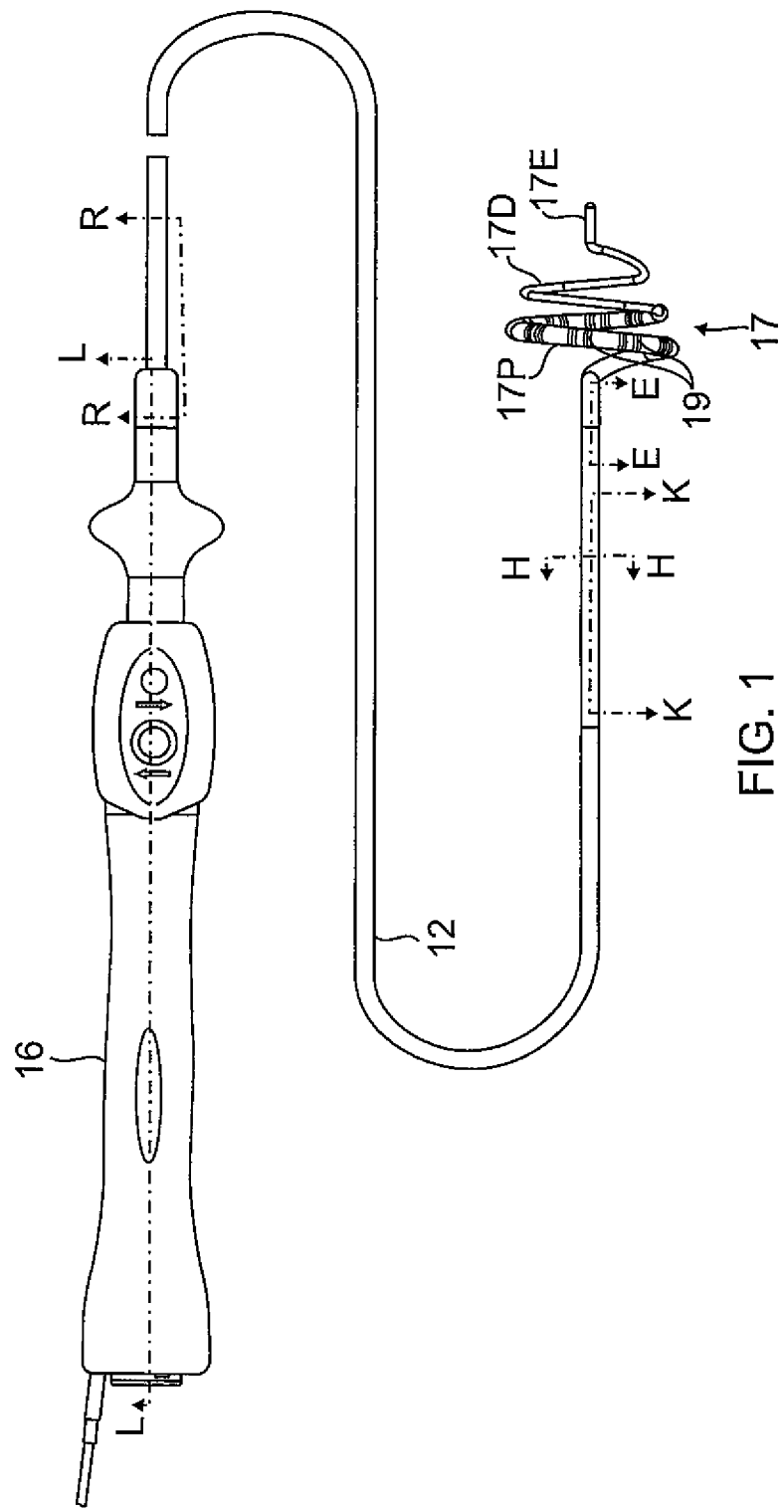
FIG. 1 is a top plan view of a catheter of the present invention, in accordance with some embodiments.
Figure 3:
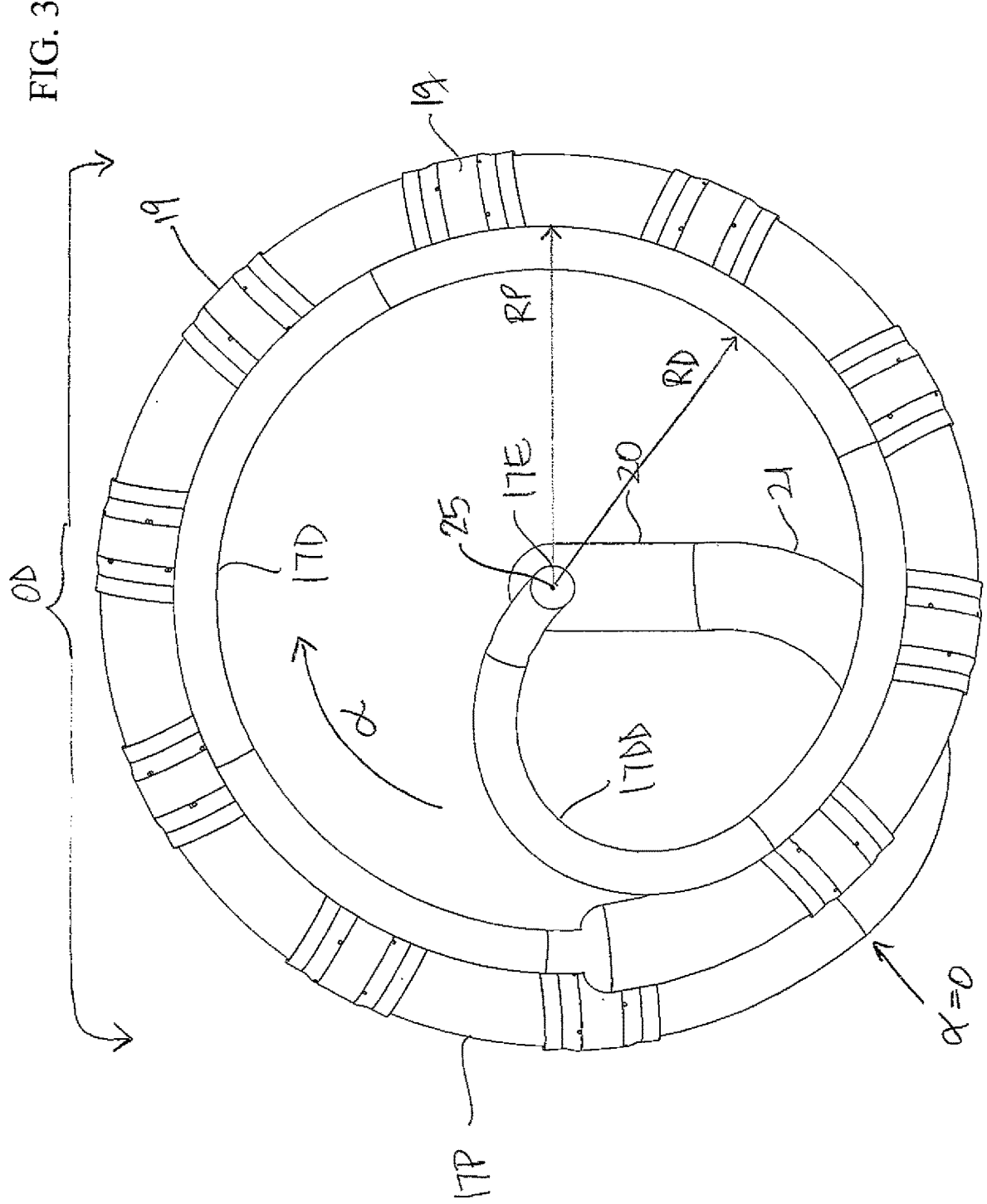
FIG. 3 is an end view of the distal assembly of FIG. 2.

Referring to FIGS. 1 and 2, a catheter 10 according to the disclosed embodiments comprises an elongated body that may include an insertion shaft or catheter body 12 having a longitudinal axis, and an intermediate section 14 distal of the catheter body that can be uni- or bi-directionally deflected off axis from the catheter body longitudinal axis. A resilient three-dimensional distal assembly 17, with ring electrodes 19 disposed along a nonlinear or curved distal portion, extends from the elongated body 12 or the intermediate section 14. In accordance with a feature of the present invention, the curved distal portion 17 defines, when unconstrained, a generally helical form 22. The helical form is oriented obliquely relative to a longitudinal axis 25 of the catheter 10 extending from the intermediate section 14. The term "obliquely", in the context of the present invention means that the plane P in space that best fits the helical form is angled relative to the longitudinal axis 25. An angle θ between the plane P and the axis 25 ranges between about 45 to 105 degrees, preferably between about 75 to 105 degrees, and more preferably about 90 degrees. Moreover, the helical form 22 of the distal assembly 17 spirals or subtends in a predetermined manner. The helical form 22 of the distal assembly 17 is advantageously centered or on-axis relative to the longitudinal axis 25 and is tapered for improved tissue contact and annular motion, as best seen in FIG. 3.

Figure 4A:
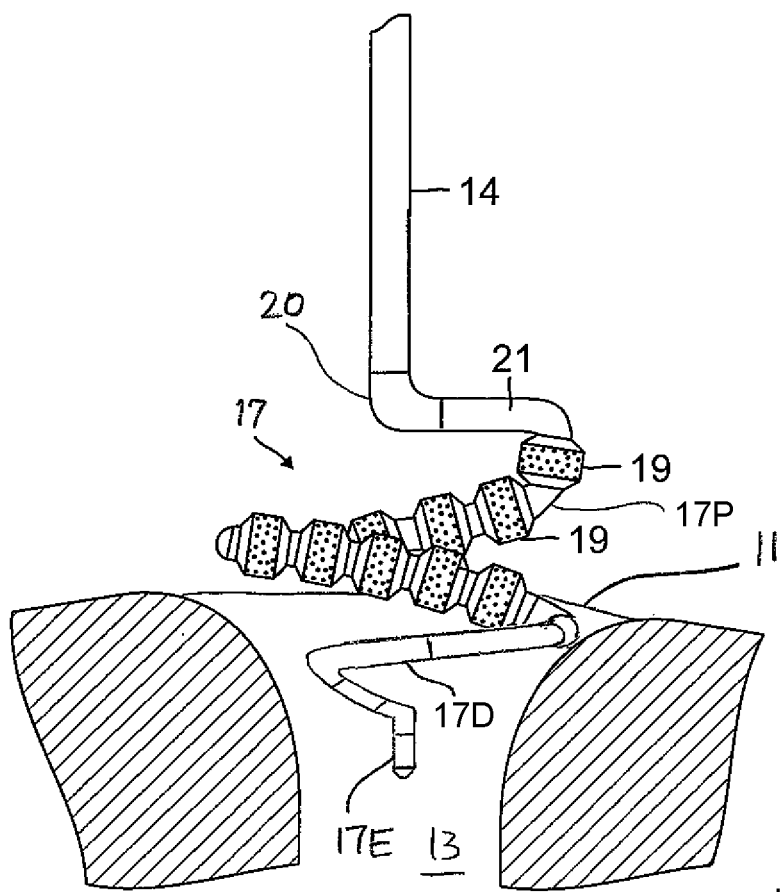
FIG. 4A is a side view of a distal assembly approaching an ostium, according to some embodiments of the present invention.
Figure 4B:
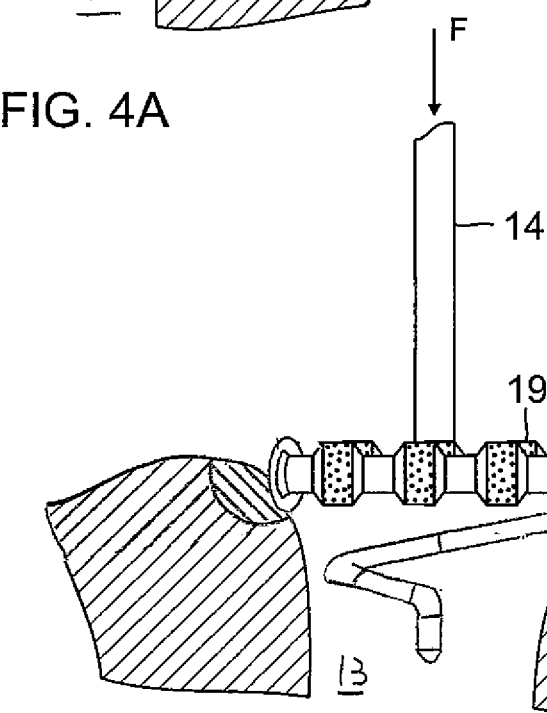
FIG. 4B is a side view of the distal assembly of FIG. 4A in contact with the ostium.

The distal assembly 17 has an electrode-carrying proximal loop 17P, and a soft "pigtail" that includes a distal loop 17D and a distal straight end section 17E, wherein the distal loop 17D and the distal straight end section 17E have a greater resiliency than the resiliency of the electrode-carrying proximal loop 17P. The pitch of the helical form 22 of the distal assembly 17 is selected to provide a gentle pressure for ensuring contact of all of ring electrodes 19 with tissue. As shown in FIGS. 4A and 4B, tapering of the helical form 22 ensures that the smaller distal loop 17D can fit into the tubular region or pulmonary vein which ensures placement of accuracy of the larger proximal loop 17P and the ring electrodes 19 carried thereon at an ostium 11 of the tubular region 13, e.g., a pulmonary vein. The greater flexibility of the distal loop 17D and the distal straight end section 17E provides an atraumatic leading element that guides distal assembly 17 into the tubular region or pulmonary vein and ensures placement accuracy of the distal assembly.

The catheter enters a patient's body through a guiding sheath that has been inserted in a body cavity, such as a heart chamber. Due to the flexible construction of the distal assembly 17, the helical form 22 readily straightens for insertion into the guiding sheath. The distal assembly is advanced axially in the guiding sheath until it moves past the distal end of the guiding sheath toward a tissue in the body, such as the inner heart wall. (The term "axial" refers to the direction along or parallel to the longitudinal axis of the catheter). When exposed and unconstrained, the distal assembly 17 reassumes the helical form 22 which is maneuvered to engage the tissue surface frontally with some or all of the ring electrodes 19 on the proximal loop 17P contacting the tissue surface simultaneously, as shown in FIGS. 4A and 4B. In accordance with the present invention, the straight distal end section 17E facilitates entry of the distal loop 17D into a tubular region by guiding the helical form 22 into the tubular region, whereupon the distal loop 17D is placed deeper into the tubular region to stabilize the placement of the proximal loop 17P and ring electrodes 19 on the ostium. The "softness" or resiliency of the distal loop 17D and the straight distal end section 17E renders these structures atraumatic so as to minimize the risk of tissue damage from any axial misalignment with the tubular region as these structures enter the tubular region. Moreover, as a user applies axial force to the catheter to push the distal assembly 17 against the ostium for better tissue contact, the distal loop 17D and the distal end section 17E positioned deeper in the tubular region minimize the risk of the proximal loop 17P slipping off the ostium, especially where the approach or the placement of the distal assembly 17 is off angle and not directly "head-on." As discussed in detail further below, if the ostium is smaller in diameter than the proximal loop 17P in its natural relaxed state, the operator can contract the proximal loop 17P by means of a contraction wire manipulated via the control handle.

Figure 5A:
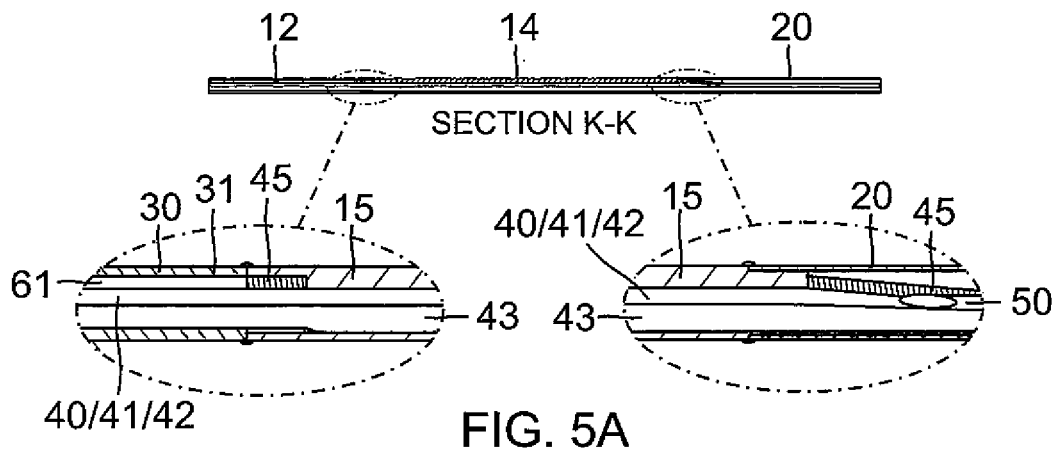
FIG. 5A is a side cross-sectional view of the catheter of FIG. 1, taken along line K-K at a junction between a catheter body and an intermediate deflection section, along a first diameter.
Figure 5B:
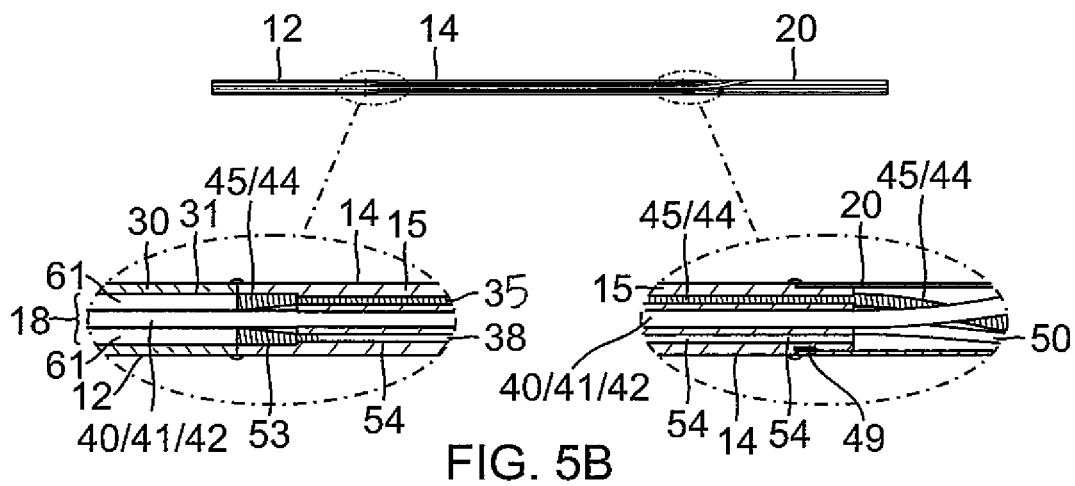
FIG. 5B is a side cross-sectional view of the junction of FIG. 5A, along a second diameter generally perpendicular to the first diameter.

In the depicted embodiment of FIGS. 5A and 5B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal assembly 17 will rotate in a corresponding manner.

The outer diameter of the catheter body 12 is not critical, but is preferably no more than about 8 french, more preferably 7 french. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

Figure 6:
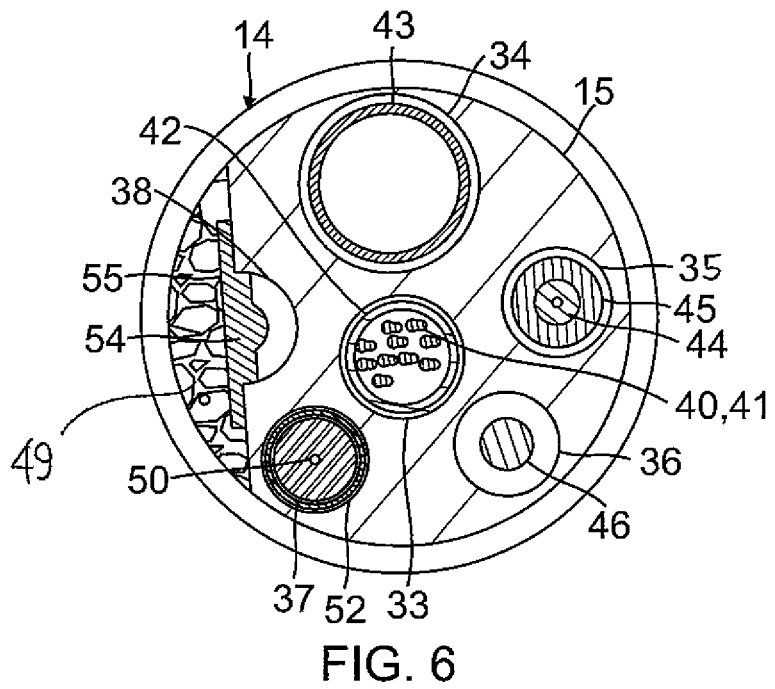
FIG. 6 is an end cross-sectional view of the catheter of FIG. 1, taken along line H-H.

The deflectable intermediate section 14 comprises a short section of tubing 15 having multiple lumens, each occupied by the various components extending through the intermediate section. In the illustrated embodiment of FIG. 6, there are six lumens. Lead wire/thermocouple pairs 40, 41 for each ring electrode pass through a first lumen 33. A non-conductive protective sheath 42 may be provided. Irrigation tubing 43 for delivering irrigation fluid to the distal assembly 17 passes through a second lumen 34. A contraction wire 44 passes through a third lumen 35. A cable 46 for a location sensor assembly 48, including a plurality of single axis sensors (SAS) positioned on the distal assembly 17, passes through a fourth lumen 36. For the distal assembly 17, a shape-memory support member 50 surrounded by a non-conductive tubing 52, e.g., a polyimide tubing, extends proximally from the distal assembly 17 for a relatively short distance into a fifth lumen 37. A puller wire 54 for deflecting the intermediate section 14 passes through a sixth lumen 38.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the position of the third lumen 35 for the distal assembly contraction wire 44 is preferably more aligned with an inner circumference of the proximal loop 17P of the distal assembly 17 so that proximal movement of the wire can readily contract the proximal loop 17P. Moreover, the sixth lumen 38 for the deflection wire 54 is off-axis so that distal movement of the deflection wire relative to the catheter accomplishes deflection toward the side on which lumen is off axis. Preferably, the third and sixth lumens 35 and 38 are diametrically opposed to each other.

The useful length of the catheter, i.e., that portion that can be inserted into the patient's body excluding the distal assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A means for attaching the catheter body 12 to the intermediate section 14 is illustrated in FIGS. 5A and 5B. The proximal end of the intermediate section 14 comprises an inner circumferential notch that receives the outer surface of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Distal the intermediate section 14 is the distal assembly 17. As shown in FIGS. 2 and 3, the distal assembly 17 includes an angled elbow section 20 immediately distal of the distal end of the intermediate section 14 and a transverse curved section 21 that form a proximal portion of the helical form 22. The elbow section 20 has an angle β of about 90 degrees and the transverse curved section 21 subtends an angle α of about 135 degrees in the radial direction and an angle θ of about 105 degrees from the longitudinal axis 25. These structures and angles enable the helical form 22 of the distal assembly 17 to be axially centered ("on axis") and obliquely angled relative to the longitudinal axis 25. The helical form 22 is therefore mounted on the catheter in an "off-edge" configuration, where longitudinal axis 25 of the intermediate section 14 does not intersect the circumference of the helical form 22 but rather extends through the interior of the helical form 22, as best shown in FIG. 3. In accordance with a feature of the present invention, the helical form 22 of the distal assembly 17 is tapered along its length by spiraling inwardly with a decreasing radius from its proximal end to its distal end, also best shown in FIG. 3.

With reference to FIGS. 2 and 3, the helical form 22 of the distal assembly 17, in some embodiments, subtends about at least about 720 degrees and preferably about 765 degrees. The proximal loop 17P subtends from the distal end of the curved section 21 at least 360 degrees, and preferably about 405 degrees, and the distal loop 17D subtends from the distal end of the proximal loop 17P at least about another 360 degrees before its distal end 17DD curves sharply inwardly toward the longitudinal axis 25 and is joined by the distal straight end section 17E which is on-axis with the longitudinal axis 25.

The helical form 22 can be defined by a radius r and a pitch P (number of 360 degreed turns per unit length along its longitudinal axis 25). The diameter suitable for mapping or ablating a PV ostium can range between about 20 mm and 35 mm. The pitch can range between about 0.5" (one 360 degree turn per 0.5 inch) and 0.3" (one 360 degree turn per 0.3 inch). With the helical form 22 tapering from its proximal end to its distal end, the radius decreases from RP its proximal end to its distal end RD (wherein RP>RD). The pitch P may remain constant between the proximal end and the distal end of the helical form, or the pitch may vary therebetween, with a greater pitch in the proximal loop 17P and a lesser pitch in the distal loop 17D, or vice versa, as needed or desired. It is understood that the helical form 22 may curve or spiral in the clockwise or counterclockwise direction. In some embodiments, the proximal loop 17P has an outer diameter OD preferably ranging to about 33 mm to about 35 mm. The elbow section 20 has an exposed length ranging between about 4 mm and 6 mm and preferably of about 5 mm. The curved transverse section 21 has an exposed length ranging between about 5 mm and 7 mm, and preferably of about 6 mm. The helical form 22 from a proximal end of the proximal loop 17P (angle α=0) to a distal end of the straight distal end section 17E has an exposed length ranging between about 18 mm and 22 mm, and preferably about 20 mm.

Figure 7:
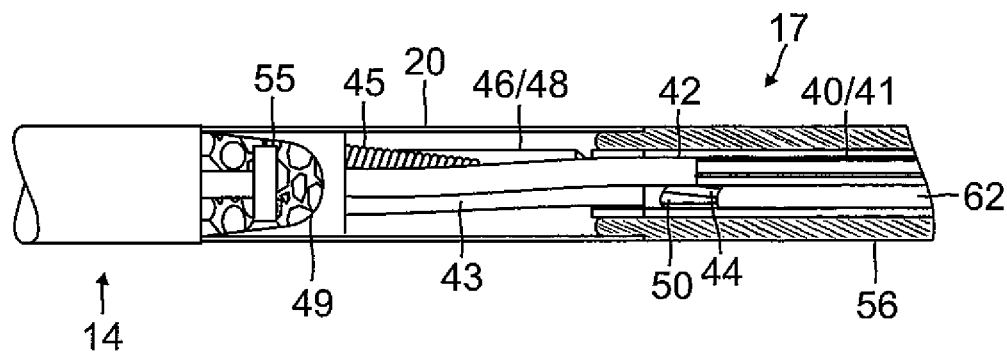
FIG. 7 is a side cross-sectional view of the catheter of FIG. 1, taken along line E-E at a junction between the intermediate deflection section and the distal assembly.

The elbow section 20, the curved section 21 and the proximal loop 17P of the distal assembly 17 are formed of multi-lumened tubing 56 which can be preformed with a desirable shape, including the helical form, as understood by one of ordinary skill in the art. A means for attaching the tubing 56 to the tubing 15 of the intermediate section 14 is shown in FIG. 7. An outer circumferential notch is made at the proximal end of the tubing 56 which is received in the distal end of the tubing 15.

In the illustrated embodiment of FIG. 2A, the tubing 56 has four off-axis lumens, namely, a first lumen 57 for the cable 46 and the SAS 48, a second lumen 58 for the ring electrode wire pairs 40, 41, a third lumen 59 for irrigation fluid, and a fourth lumen 60 for the support member 50 and the contraction wire 44. Again, position and sizing of the lumens is not critical, except the position of the fourth lumen 60 for the contraction wire 44 is preferably on an inner circumference of the proximal loop 17P so that proximal movement of the wire 44 can readily contract the proximal loop. The tubing 56 can be made of any suitable material, and is preferably made of a biocompatible plastic such as polyurethane or PEBAX.

In the depicted embodiment, the pre-formed support or spine member 50 of the distal assembly 17 extends through the fourth lumen 60 of the tubing 56 to define the shape of the helical form 22. The support member 50 is made of a material having shape-memory, i.e., that can be straightened or bent out of its original shape upon exertion of a force and is capable of substantially returning to its original shape upon removal of the force. A particularly preferred material for the support member 50 is a nickel/titanium alloy. Such alloys typically comprise about 55% nickel and 45% titanium, but may comprise from about 54% to about 57% nickel with the balance being titanium. A preferred nickel/titanium alloy is Nitinol, which has excellent shape memory, together with ductility, strength, corrosion resistance, electrical resistivity and temperature stability.

The support member 50 has a cross-section of a predetermined shape that may be generally circular or generally rectangular, including a square shape. It is understood that a generally rectangular cross section can provide greater stiffness compared to a circular cross-section of a comparable size. Moreover, the support member can have a varying thickness along its length, for example, being thinner distally and thicker proximally so that a distal portion can be more readily contracted and a proximal portion can better withstand the load from an axial force that is applied when the distal assembly 17 comes into contact with target tissue.

In some embodiments, the support member 50 has a proximal end positioned just proximal of the junction between the intermediate section 14 and the elbow section 20, for example, about 2-3 mm proximal of the junction in the fifth lumen 37. Alternatively, the support member 50 can extend further proximally into the intermediate section 14, the catheter body 12 via the central lumen 18, or further into the control handle 16, as desired or appropriate. In either instance, a nonconductive protective tubing 62 (e.g., a braided polyimide tubing) is provided in surrounding relationship with the support member 50 along its length.

In some embodiments, the support member 50 has a distal end generally coterminous with the distal end of the proximal loop 17P. In another embodiment, as discussed further below, the support member 50 extends distally, at least into the distal loop 17D, if not also and the straight distal end section 17E and has a distal end generally coterminous with the distal tip of the distal end section 17E.

The contraction wire 44 is provided to contract the proximal loop 17P to reduce its diameter. The contraction wire 44 has a proximal end anchored in the control handle 16, which is used to manipulate the contraction wire. The contraction wire 44 extends through the central lumen 18 of the catheter body 12, the third lumen 35 of the intermediate section 14, the central lumen of the elbow section 20 and the curved transverse section 21, and the fourth lumen 60 of the proximal loop 17P to its distal end. In the fourth lumen 60 of the proximal loop 17P, the contraction wire 44 extends through the nonconductive protective tubing 62 along with the support member 50. As mentioned, the fourth lumen 60 of the proximal loop 17P is positioned on the side of the proximal loop 17P closer to its center. With this arrangement, contraction of the proximal loop 17P is dramatically improved over arrangements where the position of the contraction wire 44 is not so controlled.

In some embodiments, the nonconductive protective tubing 62 comprises three layers, including an inner layer of polyimide over which a braided layer is formed, the braided layer comprising a braided stainless steel mesh or the like, as is generally known in the art. The braided layer enhances the strength of the tubing, reducing the tendency for the contraction wire 44 to straighten the preformed curve of the proximal loop 17P. A thin plastic layer of polytetrafluoroethylene is provided over the braided layer to protect the braided layer. The plastic tube 62 has a proximal end anchored to the distal end of the intermediate section 14.

Figure 8:
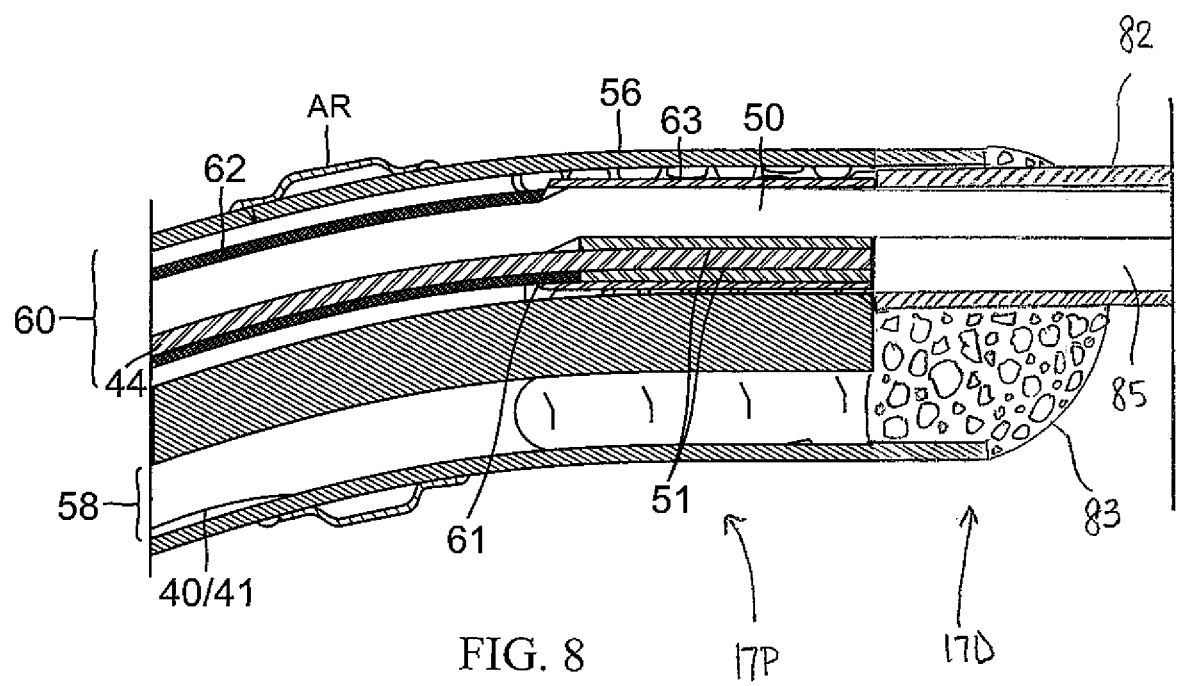
FIG. 8 is a side cross-sectional view of a junction between a proximal loop and a distal loop of the distal assembly of the catheter of FIG. 1.

The support member 50 and the contraction wire 44 extend through the protective tubing 62. In the illustrated embodiment of FIG. 8, the distal ends of the support member 50 and the contraction wire 44 (anchored in a crimped ferrule 51) are soldered or otherwise attached to a small stainless steel tube 63 which is affixed to the distal end of the fourth lumen 60 of the tubing 56 by adhesive. With this arrangement, the relative positions of the contraction wire 44 and the support member 50 can be controlled so that the contraction wire 44 can be positioned on the inner side of the proximal loop 17P closer to the center of the proximal loop 17P, as described above. The contraction wire 44 on the inside of the curve pulls the support member 50 to the inside of the curve, enhancing contraction of the helical form. Further, when the protective tubing 62 includes a braided layer, it minimizes the risk of the contraction wire 44 tearing through the multi-lumen tubing 56 of the proximal loop 17P With reference to FIG. 8, the distal loop 17D and distal straight end section 17E include nonconductive outer covering or tubing 82. The tubing provides a lumen 85 through which the support member 50 extends at least a short distance, e.g., about 10 mm, distally into the distal loop 17D to help secure the distal loop 17D to the proximal loop 17P. In other embodiments, the support member 50 may extend further into the distal loop 17D or even further into the distal end section 17E to provide their respective helical and straight shapes. It is understood that the tubing 82 may also be preformed, e.g., by heating, so that it can assume the helical and straight shapes without the support member 50 extending therethrough. In the illustrated embodiment, the tubing 82 has a smaller size or french than the tubing 56 for the proximal loop 17P. A means for attaching the tubing 82D of the distal loop 17D to the distal end of the proximal loop 17P is shown in FIG. 8. A proximal end of the tubing 82 is received in a trepanned distal end of the tubing 56, and a sealant 83, such as polyurethane, is applied to the distal end to form a junction that seals the lumens of the tubing 56 at its distal end and attaches the tubing 82D to the tubing 56.

The tubing 56 of the proximal loop 17P and the tubing 82 of the distal loop 17D may be made of any suitable material, for example, polyurethane or PBEXA. In accordance with a feature of the present invention, the material of the tubing 56 has a durometer that is equal or greater than the durometer of the material of the tubing 82, so that the distal loop 17D is softer and has greater resiliency than the proximal loop 17P even if the support member 50 extending through the proximal loop 17P also extends the entirety of distal loop 17D.

With reference to FIGS. 5A and 5B, the compression coil 45 surrounding the contraction wire 44 extends from the proximal end of the catheter body 12 and through the third lumen 35 of the intermediate section 14. The compression coil has a distal end at or near the distal end of the intermediate section 14. The compression coil 45 is made of any suitable metal, preferably stainless steel, and is tightly wound on itself to provide flexibility, i.e., bending, but to resist compression. The inner diameter of the compression coil is preferably slightly larger than the diameter of the contraction wire 44. The outer surface of the compression coil is covered by a flexible, non-conductive sheath, e.g., made of polyimide tubing. The compression coil preferably is formed of a wire having a square or rectangular cross-sectional area, which makes it less compressible than a compression coil formed from a wire having a circular cross-sectional area. As a result, the compression coil 45 keeps the catheter body 12, and particularly the intermediate section 14, from deflecting when the contraction wire 44 is manipulated to contract the distal assembly 17 as it absorbs more of the compression.

Figure 9:
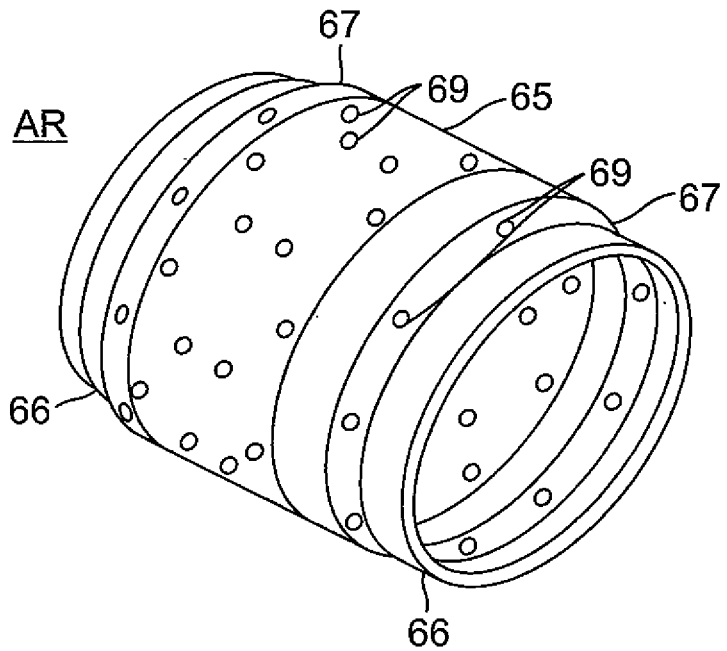
FIG. 9 is a perspective view of an embodiment of an irrigated ablation electrode.
Figure 10:
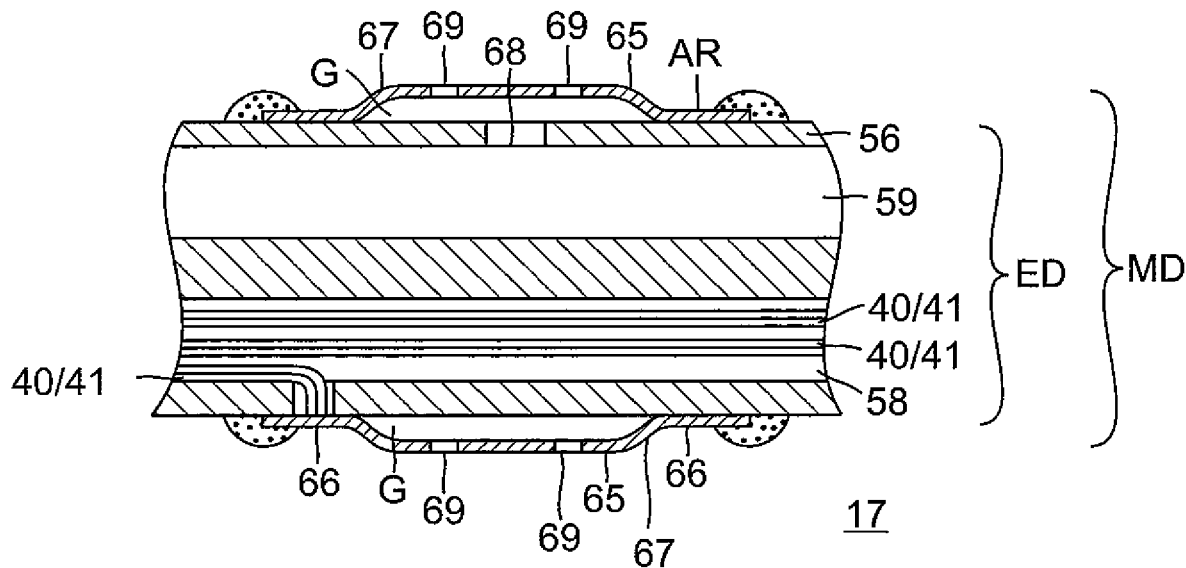
FIG. 10 is a side cross-sectional view of a portion a proximal loop and an irrigated ablation electrode mounted thereon of the catheter of FIG. 1.

A plurality of ring electrodes 19 are mounted on predetermined locations on the proximal loop 17P, as shown in FIG. 2. The electrodes can be made of any suitable solid conductive material, such as platinum or gold, preferably a combination of platinum and iridium or gold and platinum, and mounted onto the tubing with glue or the like. A suitable embodiment of an electrode adapted for ablation and irrigation is illustrated in FIGS. 9 and 10. The ablation reservoir ("AR") electrode is generally cylindrical with a length greater than its diameter. In some embodiments, the length is about 3.0 mm, the outer diameter is about 2.8 mm, and the inner diameter is about 2.33 mm.

In the illustrated embodiment, the AR electrode has a side cross-section that can resemble a barrel with a side wall 65 (with a width, in some embodiments, of about 2.5 mm) that bulges radially such that a mid portion diameter MD is greater than end diameter ED at opposing end portions 66. Curved transitional regions 67 are provided between the side wall 65 and the end portions 66 to provide an atraumatic profile without corners or sharp edges.

Notably, the mid portion diameter is greater than the outer diameter of the underlying tubing 56 of the distal assembly so that a reservoir or annular gap G exists around the exterior of the tubing 56. The gap G provides improved fluid distribution from the third lumen 59 to the exterior of the AR electrode via an opening 68 provided in the outer wall of the tubing 56 and apertures 69 strategically formed and positioned in the side wall 65 of the AR electrode. The size of the opening 68 in the tubing 56 varies with the position along the length of the proximal loop 17P. For optimum flow, the more distal an opening is along the helical form, the greater the size or cross-section of the opening and/or the plurality of openings for each AR electrode.

The apertures 69 are arranged the side wall 65 of an AR electrode in a predetermined pattern including axially offset rows. These apertures face outwardly promoting flow in a radial direction. Apertures are also provided in or near the curved transitional regions 67 to promote flow in an axial direction. Moreover, these apertures are particularly effective in minimizing charring and coagulation at or near the curved transitional regions which are likely to be "hot spots" resulting from higher current densities due to transitions in the electrode profile. In that regard, the plurality and/or cross-section of the apertures is greater at or near the curved transitional regions than in the side wall of the electrode so as to provide more cooling in the curved transitional regions. As such, the catheter can deliver more irrigation and consequently more cooling without increasing overall flow rate and overall fluid load on the patient.

In some embodiments, there are about 10 apertures on each end portion 66 and about 20 apertures on the side wall 65. The pattern may be adjusted to further improve the flow distribution from each AR electrode. The pattern can be adjusted by adding or removing apertures, modifying the spacing between the apertures, modifying the location of the apertures on the ring electrodes and/or modifying the aperture geometry. Other suitable ring electrodes are described in the aforementioned U.S. Pat. No. 8,475,450, issued Jul. 2, 1013.

Irrigation fluid is delivered to the distal assembly 17 by the irrigation tubing 43 whose proximal end is attached to a luer hub (not shown) proximal of the control handle 16 and receives fluid delivered by a pump (not shown). The irrigation tubing extends through the control handle 16, the central lumen 18 of the catheter body 12, the second lumen 34 of the intermediate section 14, the central lumen of the transitional section 20 and a short distance distally into the third lumen 59 of the proximal loop 17P, for example, about 5 mm. The fluid enters the third lumen 59 where it exits the lumen via the openings 68 into the reservoir R of the AR electrodes where it exits the reservoir via the apertures 69 to outside of the AR electrodes to minimize charring.

The number of AR electrodes on the proximal loop 17P can vary as desired. Preferably the number of AR electrodes ranges from about six to about twenty, more preferably from about eight to about twelve. In some embodiments, the proximal loop 17P carries ten AR electrodes. The electrodes can be approximately evenly spaced around the proximal loop 17P, as shown in FIG. 7.

Figure 14:
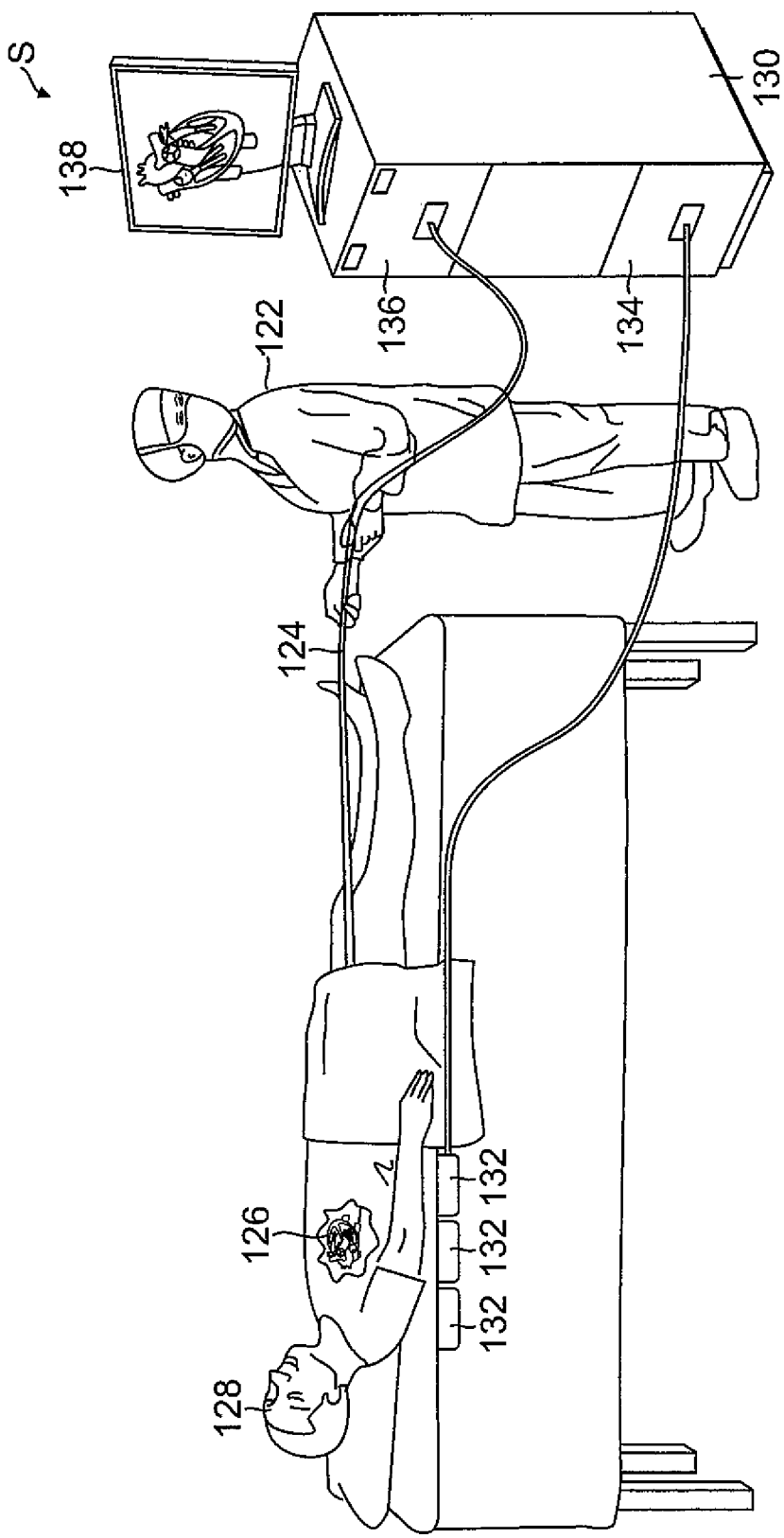
FIG. 14 is a schematic pictorial illustration of a system for ablation of tissue in the heart, in accordance with an embodiment of the present invention.

The proximal end of each wire is electrically connected to a suitable connector (not shown) distal of the control handle 16 for transmitting and/or receiving electrical signals to accomplish ablation. Each AR electrode is connected to a respective pair of wires 40, 41. In the disclosed embodiment, wire 40 of the wire pair is a copper wire, e.g. a number "40" copper wire. The other wire 41 of the wire pair is a constantan wire. The wires of each pair are electrically isolated from each other except at their distal ends where they are twisted together, fed through a hole formed in the second lumen 58 of the proximal loop 17P, and soldered to their respective AR electrode (FIG. 14). The wire pairs for each electrode extend from the control handle 16, through the central lumen 18 of the catheter body 12, the first lumen 33 of the intermediate section 14, the central lumen of the transitional section 20, and the second lumen 58 of the proximal loop 17P. Ablation energy, e.g., RF energy, is delivered to the AR electrodes via the wire 40 of the wire pairs. However, the wire pairs inclusive of their respective constantan wire can also function as temperature sensors or thermocouples sensing temperature of each AR electrode.

All of the wire pairs pass through one nonconductive protective sheath 42 (see FIG. 6), which can be made of any suitable material, e.g., polyimide, in surrounding relationship therewith. The sheath 42 extends from the control handle 16, the catheter body 12, the intermediate section 14, the transitional section 20 and into the second lumen 58 of the proximal loop 17P, terminating just distal of the junction between the transitional section 20 and the distal assembly 17, for example, about 5 mm into the second lumen 58. The distal end is anchored in the second lumen by glue, for example, polyurethane glue or the like.

Figure 11:
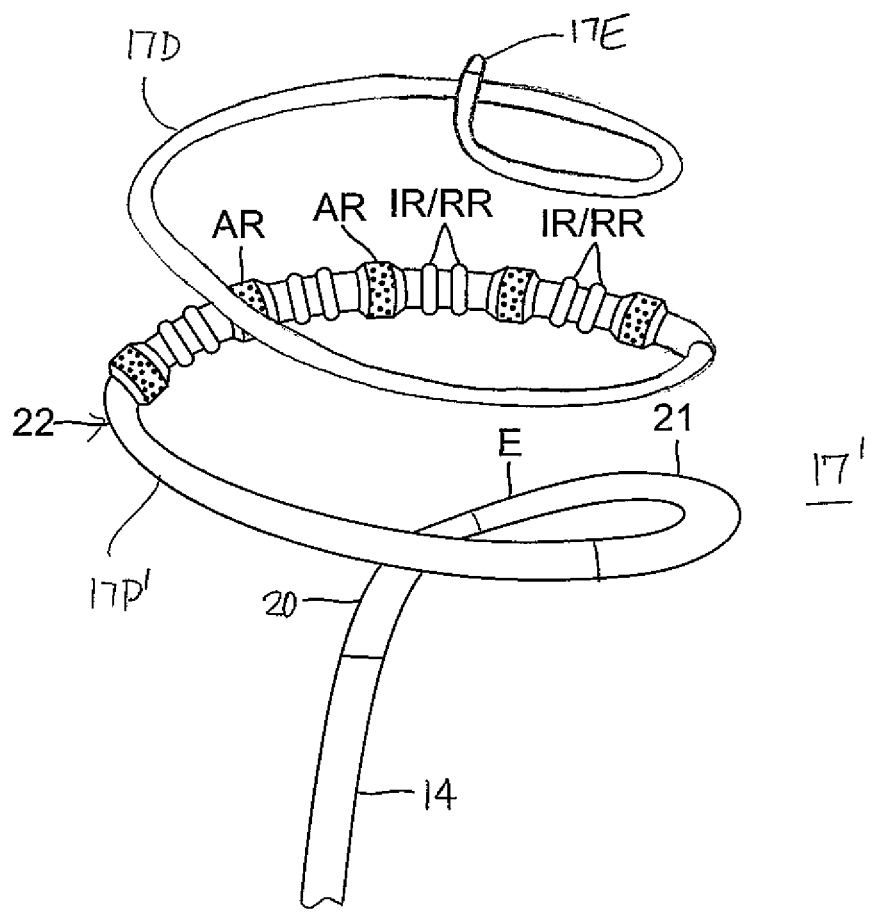
FIG. 11 is a detailed perspective view of a distal assembly, in accordance with another embodiment of the present invention.

An alternate electrode arrangement is depicted in FIG. 11. In this alternate embodiment, distal assembly 17' has five AR electrodes and includes additional ring electrodes that are narrower than the AR electrodes. Such additional ring electrodes may be impedance recording (IR) electrodes that are electrically isolated from each other and the AR electrodes, and are adapted for recording impedance. In some embodiments of the IR electrodes, the length is about 0.75 mm and the inner diameter is about 2.3 mm. The degree of success of mapping and/or ablation depends on tissue contact. Thus, tissue contact information is particularly useful with multi-electrode ablation catheters. Utilizing at least two independent pairs of IR electrodes (a "pair" hereinafter being any two electrodes, or preferably two most adjacent electrodes) with various size and spacing allows assessment of tissue contact by comparing impedance values and ratio at different frequencies/domains utilizing a single multi-electrode catheter.

The impedance can be further assessed at various frequencies/domains. For example, the ratio of impedance between a pair of IR electrodes and a pair of AR electrodes is used to assess tissue contact in terms of verifying contact and degree or amount of contact. With such isolated bi-polar IR electrodes, the catheter is adapted to perform simultaneous ablation, mapping (electrogram recording) and assessment of tissue contact.

The IR electrodes can be located in between each pair of AR electrodes or selected pairs of AR electrodes depending on the geometry of the distal assembly 17, to provide accurate tissue contact verification via a comparison of the impedance between a pair of isolated (smaller) IR electrodes and the impedance between a pair of (larger) AR electrodes. In the illustrated embodiment of FIG. 11, there are two IR electrodes between each adjacent pair of AR electrodes, for a total of 2(N−1) plurality of IR electrodes for N plurality of AR electrodes.

In another alternate embodiment as also illustrated in FIG. 11, the distal assembly 17 includes electrically isolated bi-polar recording ring ("RR") electrodes located in between the AR electrodes to provide improved visualization of pulmonary vein ("PV") potentials. The catheter with such isolated bio-polar RR electrodes permits simultaneous ablation and electrogram recording without the need to reposition the catheter. To minimize far-field effects or any decrease in visualization resolution for more precise electrogram recording of PV potentials, the narrower bi-polar RR electrodes are positioned with a predetermined spacing in between each pair of AR electrodes or in between selected pairs of AR electrodes depending upon the geometry of the distal assembly.

As understood by one of ordinary skill in the art, two closely-spaced RR electrodes allow for more accurate detection of near field PV potential versus far field atrial signals, which is very important when trying to treat atrial fibrillation. Specifically, the near field PV potentials are very small signals whereas the atria, located very close to the pulmonary vein, provide much larger signals. Accordingly, even when the distal assembly 17 is placed in the pulmonary vein, it can be difficult for the physician to determine whether the signal is a small, close potential (from the pulmonary vein) or a larger, farther potential (from the atria). Closely-spaced bipoles permit the physician to more accurately determine whether he is looking at a close signal or a far signal. Accordingly, by having closely-spaced electrodes, one is able to better target the locations of myocardial tissue that have PV potentials and therefore allows the clinician to deliver therapy to the specific tissue. Moreover, the closely-spaced electrodes allow the physician to determine the exact anatomical location of the ostium by the electrical signal.

In some embodiments, a pair of RR electrodes are provided between each adjacent pairs of AR electrodes. Thus, for an M plurality of AR electrodes, there are 2(M−1) plurality of RR electrodes. In the illustrated embodiment, the distal assembly 17 carries 10 AR electrodes with a spacing of approximately 4.0 mm between adjacent AR electrodes. Where the distal assembly 17 also carries IR or RR electrodes, they can have a spacing of 1.0 mm between each other. Additionally, the distal most AR electrode can be a different size from the other AR electrodes so as to provide a visually distinguishing signal to the user when the catheter is being viewed under fluoroscopy. Specifically, because the distal assembly 17 is generally circular, it can be difficult for the user to determine the orientation of the helical form 22 and which electrodes are placed at a particular location in the heart. By having one AR electrode, such as the most distal AR electrode, being longer, the user has a reference point when viewing the catheter under fluoroscopy.

For any additional AR or RR electrodes as described above, additional lead wire pairs 40, 41 are provided as appropriate. They extend through the second lumen 58 of the distal assembly 17, the central lumen of the connector tubing 23, the first lumen 33 of the intermediate section 14, the central lumen 18 of the catheter body 12 and into the control handle 16.

The deflection puller wire 54 is provided for deflection of the intermediate shaft 14. The deflection wire 54 extends through the central lumen 18 of the catheter body 12 and the sixth lumen 38 of the intermediate section 14. It is anchored at its proximal end in the control handle 16, and at its distal end to a location at or near the distal end of the intermediate section 14 by means of a T-bar 55 (FIGS. 6 and 7) that is affixed to the sidewall of the tubing 15 by suitable material 49, e.g., polyurethane. The distal end is anchored to the sidewall of the tubing 15 of the intermediate section as is generally described in U.S. Pat. No. 6,371,955, the entire disclosure of which is incorporated herein by reference. The puller wire 54 is made of any suitable metal, such as stainless steel or Nitinol, and is preferably coated with Teflon® or the like. The coating imparts lubricity to the puller wire. The puller wire preferably has a diameter ranging from about 0.006 to about 0.010 inch.

A second compression coil 53 is situated within the central lumen 18 of the catheter body 12 in surrounding relation to the puller wire 54 (FIG. 5B). The second compression coil 53 extends from the proximal end of the catheter body 12 to at or near the proximal end of the intermediate section 14. The second compression coil 53 is made of any suitable metal, preferably stainless steel, and is tightly wound on itself to provide flexibility, i.e., bending, but to resist compression. The inner diameter of the second compression coil 53 is preferably slightly larger than the diameter of the puller wire 54. The Teflon® coating on the puller wire allows it to slide freely within the second compression coil. Within the catheter body 12, the outer surface of the second compression coil 53 is covered by a flexible, non-conductive sheath 61, e.g., made of polyimide tubing. The second compression coil 53 is anchored at its proximal end to the outer wall 30 of the catheter body 12 by a proximal glue joint and to the intermediate section 14 by a distal glue joint.

Within the sixth lumen 38 of the intermediate section 14, the puller wire 54 extends through a plastic, preferably Teflon®, puller wire sheath, which prevents the puller wire 54 from cutting into the wall of the tubing 15 of the intermediate section 14 when the intermediate section 14 is deflected.

With reference to FIG. 1, longitudinal movement of the contraction wire 44 relative to the catheter body 12, which results in contraction of the proximal loop 17P of the distal assembly 17, is accomplished by suitable manipulation of the control handle 16. Similarly, longitudinal movement of the deflection wire 54 relative to the catheter body 12, which results in deflection of the intermediate section 14, is accomplished by suitable manipulation of the control handle 16. Suitable control handles for manipulating more than one wire are described, for example, in U.S. Pat. Nos. 6,468,260, 6,500,167, and 6,522,933, the disclosures of which are incorporated herein by reference. Suitable control handles for manipulating lasso-type catheters are described in U.S. application Ser. No. 12/550,307, filed Aug. 28, 2009 (now published as 2011/0054287 A1), and U.S. application Ser. No. 12/550,204, filed Aug. 28, 2009 (now published as 2011/0054446 A1), the entire disclosures of which are incorporated herein by reference.

Figure 12:
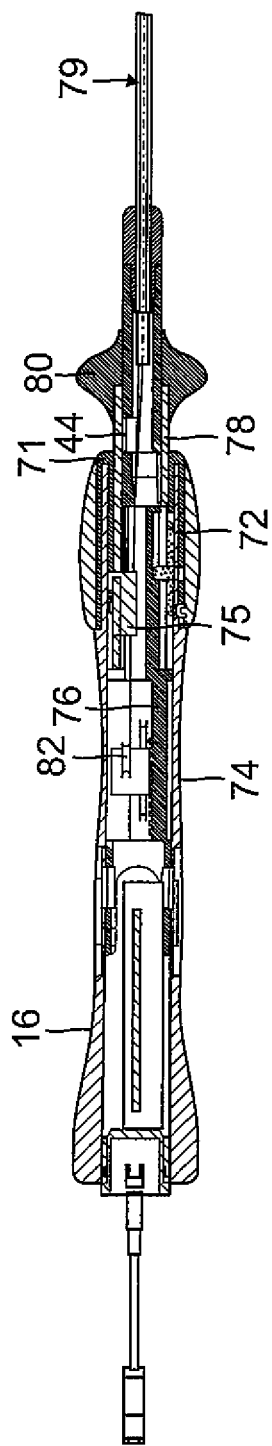
FIG. 12 is a side cross-sectional view of the control handle of FIG. 1, taken along line L-L.
Figure 13:
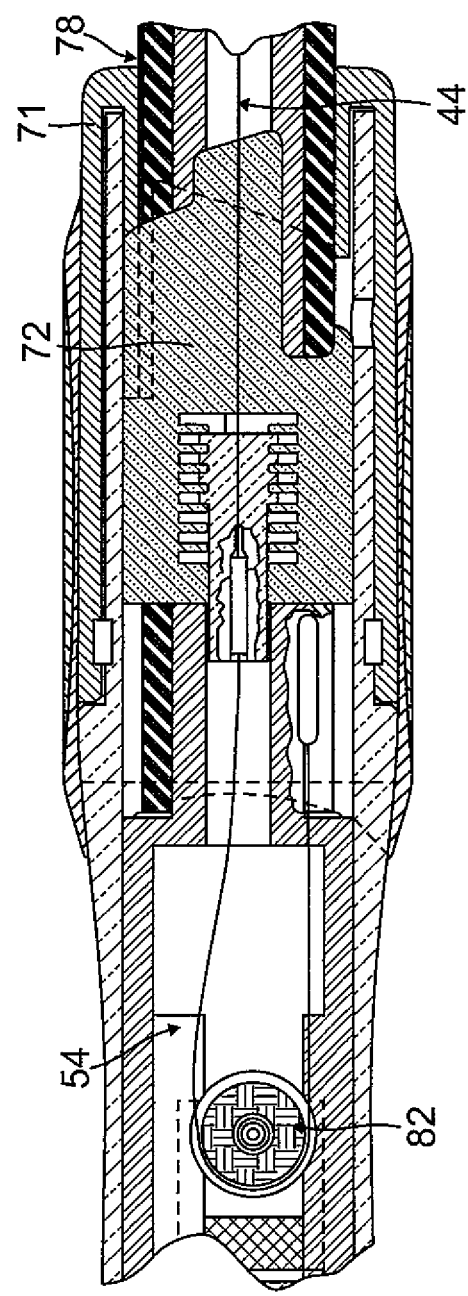
FIG. 13 is a partial detailed view of the control handle of FIG. 12.

In some embodiments, the catheter includes a control handle 16 as shown in FIGS. 12 and 13. The control handle 16 includes a deflection control assembly that has a handle body 74 in which a core 76 is fixedly mounted and a piston 78 is slidably mounted over a distal region of the core 76. The piston 78 has a distal portion that extends outside the handle body. A thumb knob 80 is mounted on the distal portion so that the user can more easily move the piston longitudinally relative to the core 76 and handle body 74. The proximal end of the catheter body 12 is fixedly mounted to the distal end of the piston 78. An axial passage 79 is provided at the distal end of the piston, so that various components, including lead wires 40, 41, contraction wire 44, deflection wire 54, sensor cable 46 and irrigation tubing 43 that extend through the catheter body 12 can pass into and if appropriate, through the control handle. For example, the lead wires 40, 41 can extend out the proximal end of the control handle 16 or can be connected to a connector that is incorporated into the control handle, as is generally known in the art.

The proximal end of the deflection wire 54 enters the control handle 16, and is wrapped around a pulley 82 and anchored to the core 76. Longitudinal movement of the thumb knob 80 and piston 78 distally relative to the handle body 74 and core 76 draws the proximal end of the deflection wire 54 distally. As a result, the deflection wire 54 pulls on the side of the intermediate section 14 to which it is anchored, thereby deflecting the intermediate section in that direction. To straighten the intermediate section 14, the thumb knob 80 is moved proximally which results in the piston 78 being moved proximally back to its original position relative to the handle body 74 and core 76.

The control handle 16 is also used for longitudinal movement of the contraction wire 44 by means of a rotational control assembly. In the illustrated embodiment, the rotational control assembly includes a cam handle 71 and a cam receiver 72. By rotating the cam handle in one direction, the cam receiver is drawn proximally to draw on the contraction wire 44. By rotating the cam handle in the other direction, the cam receiver is advanced distally to release the contraction wire. For example, where the proximal loop 17P has an original outer diameter of about 35 mm, tightening of the proximal loop 17P by means of the contraction wire can reduce the outer diameter to about 20 mm. The contraction wire 44 extends from the catheter body 12 into the control handle 16, through the axial passage in the piston 78 and through the core 76 to be anchored in an adjuster 75 by which tension on the contraction wire can be adjusted.

In some embodiments, the position sensor 48 includes a plurality of single axis sensors ("SAS") carried on the cable 46 that extends through the first lumen 57 of the distal assembly 17 (FIG. 2A), where each SAS occupies a known or predetermined position on the proximal loop 17P. The cable 46 extends proximally from the distal assembly 17 through the central lumen of the transitional section 20, the fourth lumen 36 of the intermediate section 14 (FIG. 6), the central lumen 18 of the catheter body 12, and into the control handle 16. Each SA sensor can be positioned with a known and equal spacing separating adjacent SASs. In the disclosed embodiment, the cable carries three SASs that are positioned under the distal-most AR electrode, the proximal-most AR electrode, and a mid AR electrode, for sensing location and/or position of the proximal loop 17P. Where the distal assembly carries ten AR electrodes, the SASs are under electrodes AR1, AR5 and AR10 (FIG. 7). The SASs enable the proximal loop 17P to be viewed under mapping systems manufactured and sold by Biosense Webster, Inc., including the CARTO, CARTO XP and NOGA mapping systems. Suitable SASs are described in U.S. application Ser. No. 12/982,765, filed Dec. 30, 2010 (now published as 2012/0172703 A1), the entire disclosure of which is incorporated herein by reference.

In an alternative embodiment of the present invention as illustrated in FIG. 11, distal assembly 17' includes an electrode-carrying proximal loop 17P' of which only a portion thereof (e.g., the distal semi-circular portion of loop 17P') carries AR electrodes 19. The proximal loop 17P' has generally the same structure and construction as the proximal loop 17P, but the electrode-carrying portion thereof subtends an angle no greater than about 180 degrees. The distal assembly 17' is particularly useful where the patient has a larger PV ostium or where two PV are in such close proximity to each other that they share a common ostium.

The present catheter 10 is a steerable, multi-electrode, irrigated luminal catheter. The catheter is deployed in a target region of the body, e.g., the atria of the heart, through a guiding sheath. The catheter is designed to facilitate electrophysiological mapping of the target region, e.g., the atria, and to transmit energy, e.g., radiofrequency (RF) current, to the catheter electrodes for ablation purposes. For ablation, the catheter is used in conjunction with a multi-channel RF generator and irrigation pump.

The configuration of the catheter permits the catheter to sit at an opening of a tubular formation, e.g., the PV ostia, with consistent circumferential contact with the tissue. Intra-cardia signals are recorded by an EP Recording System and the location of the catheter is visualized by fluoroscopy. Once the catheter is in the desired location, energy is delivered (to multiple electrodes simultaneously or selectively) to the veins ostium in unipolar or bipolar mode resulting in PV isolation.

In some embodiments, ablation is delivered at a set wattage on the multi-channel RF generator. During ablation the multi-channel RF generator monitors the temperature of the ring electrode(s) involved and reduces the wattage if the temperature exceeds a value set by the user. The multi-channel RF generator routes the RF current through the selected ring electrodes and catheter temperature information is sent from the thermocouple on the catheter to the generator.

During ablation, an irrigation pump is used to deliver normal heparinized saline to the ring electrodes to cool the ring electrodes to prevent blood from coagulating. The apertures in the ring electrodes facilitate irrigation of the ablation areas of the catheter. Where deeper lesions are desired, the greater flow distribution (without greater flow rate) of each ring electrode via the apertures reduces the increased risk of charring and coagulum on the ablation surfaces that would normally be encountered when the amount of power delivered to the electrode/tissue interface is increased. A greater flow distribution from each ring electrode which leads to improved irrigation efficiency offers advantages, including (1) higher power delivery without increasing fluid pump flow rate, (2) ability to use currently available, flow rate-limited pumps, (3) eliminate need to use multiple pumps, and/or (4) reduction in fluid load on patient during ablation procedure.

Figure 16:
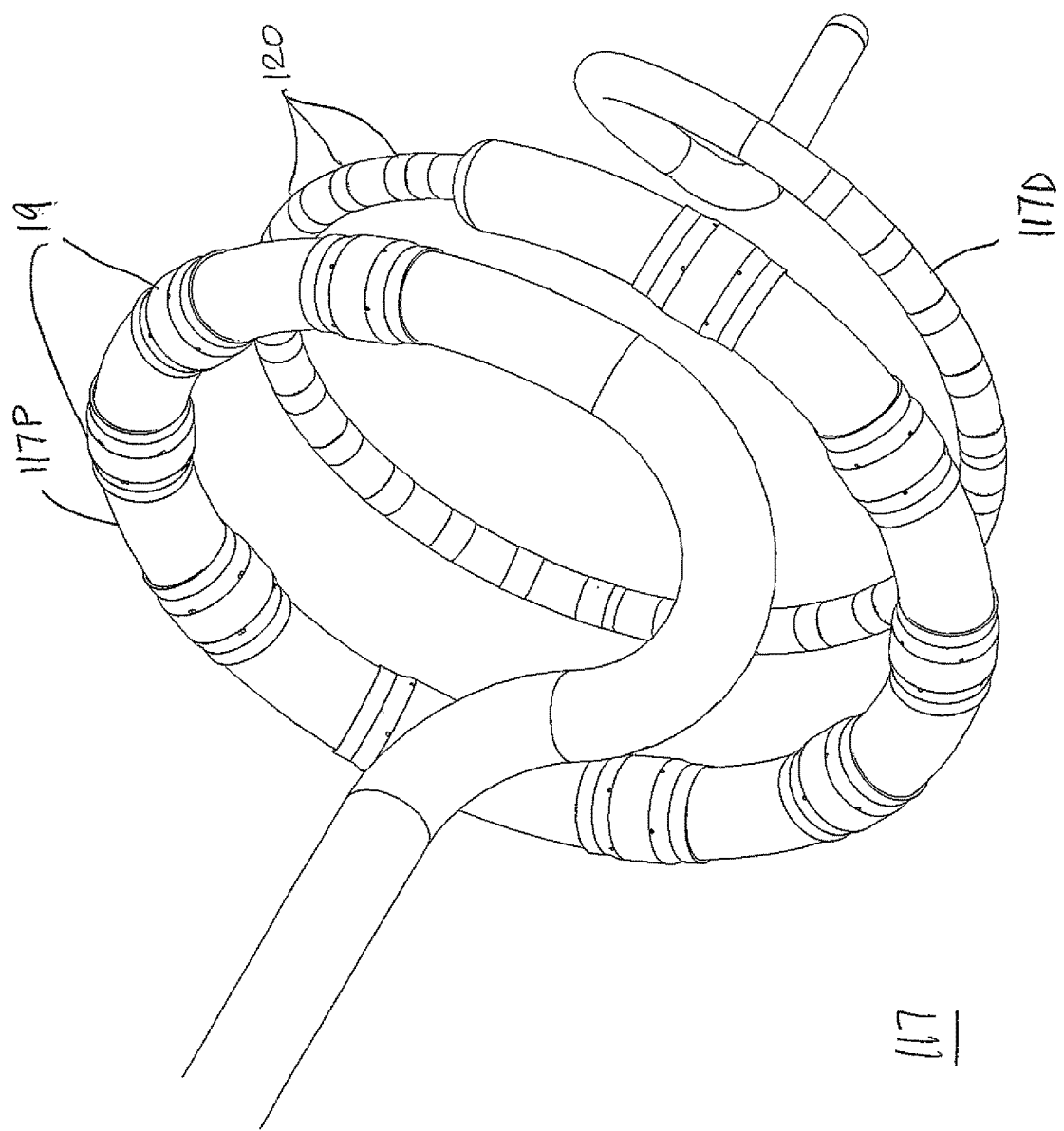
FIG. 16 is a detailed perspective view of a distal assembly, in accordance with yet another embodiment of the present invention.

FIG. 16 illustrates a distal assembly 117 in accordance with another embodiment of the present invention. The distal assembly 117 has generally the same structure and construction as the above-described distal assembly 17 but soft distal loop 117D provide diagnostic capabilities by carrying a plurality of ring electrodes 120 adapted for unipolar and/or bipolar sensing of electrical potentials for electrogram recording without the need to reposition the catheter. Properly spaced, narrow recording electrodes 120 on the distal loop allows for precise visualization of electrical potentials within the tubular region. The plurality of ring electrodes 120 ranges between about 10 to 40, preferably about 14 to 30, and more preferably about 20. Accordingly, the distal assembly 117 is particularly useful for the treatment of atrial fibrillation where, for example, errant electrical activity enters the left atrium from a pulmonary vein, and the distal loop 117D may be safely positioned further in the pulmonary vein to detect the source of the errant electrical activity while the proximal loop 117P may be reliably positioned on the pulmonary vein ostium to ablate and block the errant electrical activity from entering the left atrium. It is understood that the tubing of the distal assembly 117 may be multi-lumened, with at least one lumen dedicated to the lead wires of the ring electrodes 120 of the distal loop 117D.

FIG. 14 is a schematic pictorial illustration of a system S for ablation of tissue in a heart 126 of a patient 128, in accordance with an embodiment of the present invention. An operator 122, such as a cardiologist, inserts a catheter 10 through the vascular system of the patient so that the distal end of the catheter enters a chamber of the patient's heart. Operator advances the catheter so that distal assembly 17 of the catheter engages endocardial tissue at a desired location or locations. Catheter 10 is connected by a suitable connector at its proximal end to a console 130. The console comprises an RF generator for applying RF energy through electrodes on the end section of the catheter in order to ablate the tissue contacted by the distal section. Alternatively or additionally, catheter may be used for other diagnostic and/or therapeutic functions, such as intracardiac electrical mapping or other types of ablation therapy.

In the pictured embodiment, system S uses magnetic position sensing to determine position coordinates of the distal assembly of the catheter inside heart. To determine the position coordinates, a driver circuit 134 in console 130 drives field generators 132 to generate magnetic fields within the body of patient. Typically, field generators comprise coils, which are placed below the patient's torso at known positions external to the body. These coils generate magnetic fields in a predetermined working volume that contains heart. One or more magnetic field sensors within the end section of catheter generate electrical signals in response to these magnetic fields. The console 130 processes these signals in order to determine the position (location and/or orientation) coordinates of the distal assembly 17 of the catheter, and possibly also the deformation of the distal assembly, as explained below. Console may use the coordinates in driving a display 138 to show the location and status of the catheter. This method of position sensing and processing is described in detail, for example, in PCT International Publication WO 96/05768, whose entire disclosure is incorporated herein by reference, and is implemented in the CARTO system produced by Biosense Webster Inc. (Diamond Bar, California).

Alternatively or additionally, system may comprise an automated mechanism (not shown) for maneuvering and operating catheter within the body of patient. Such mechanisms are typically capable of controlling both the longitudinal motion (advance/retract) and the rotation of catheter. In such embodiments, console generates a control input for controlling the motion of the catheter based on the signals provided by the position sensing system.

Although FIG. 14 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter that causes console to receive signals indicative of the coordinates of the element. The position transducer may thus comprise a received in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 15:
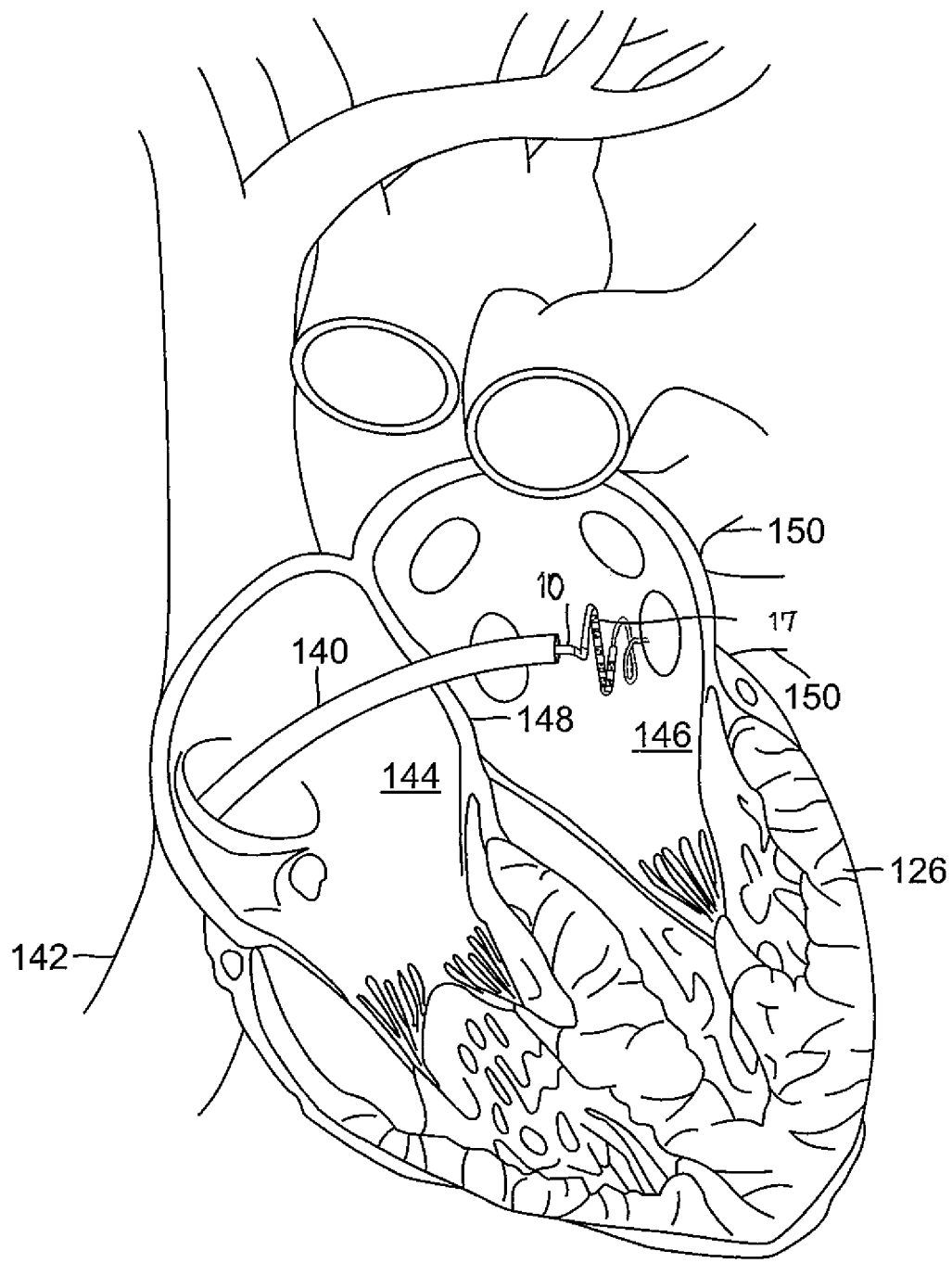
FIG. 15 is a schematic sectional view of a heart showing insertion of a catheter into the left atrium, in accordance with an embodiment of the present invention.

FIG. 15 is a schematic sectional view of heart 126, showing insertion of catheter 10 into the heart, in accordance with an embodiment of the present invention. To insert the catheter in the pictured embodiment, the operator first passes a guiding sheath 140 percutaneously through the vascular system and into right atrium 144 of the heart through ascending vena cava 142. The sheath penetrates through interatrial septum 148, typically via the fossa ovalis, into left atrium 146. Alternatively, other approach paths may be used. Catheter is then inserted through the guiding sheath until the distal assembly 17 of the catheter extends past the distal end of the guiding sheath 140 into the left atrium 146.

Operator aligns the longitudinal axis of guiding sheath 140 (and of catheter) inside left atrium 146 with the axis of one of pulmonary veins. He may use the thumb knob 80 of the control handle 16 to deflect the intermediate section 14 in directing the distal assembly 17 toward the target ostium. The operator may carry out this alignment using the position sensing methods described above, along with a pre-acquired map or image of heart. Alternatively or additionally, the alignment may be performed under fluoroscopic or other means of visualization. The operator advances the catheter toward the target tubular region or pulmonary vein 13 so that the soft distal end 17E first enters the pulmonary vein, followed by the soft distal loop 17D, both of which guide the positioning and placement of the electrode-carrying proximal loop 17P onto the ostium (FIG. 4A). The operator may apply a force F in the axial direction to press the proximal loop 17P onto the ostium to ensure contact between the ring electrodes 19 and the tissue (FIG. 4B). Advantageously, the soft distal end 17E and the soft distal loop 17D positioned further into the tubular region or pulmonary vein 13 help hold the proximal loop 17P on the ostium so it does not slip off the ostium. By manipulating the cam handle 71, the proximal loop 17P is contracted to fit the PV ostium. In the disclosed embodiment, the contraction wire 44 is drawn proximally by the cam receiver 72 to tighten and decrease the diameter of the proximal loop 17P when the cam handle is turned in one direction. By turning the cam handle in the opposition direction, the cam receiver releases the contraction wire to allow the proximal loop 17P to expand and return to its original diameter.

The operator can then rotate the catheter about its axis within the guiding sheath so that the proximal loop 17P traces an annular path around the inner circumference of the vein. Meanwhile, the operator actuates RF generator to ablate the tissue in contact with the AR electrodes along the path. Simultaneously, impedance and/or PV potential recordings can be made with the IR and/or RR electrodes. After completing this procedure around one pulmonary vein, the operator may shift the sheath and catheter and repeat the procedure around one or more of the other pulmonary veins.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in some embodiments may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated catheter body having a longitudinal axis;
   a distal assembly distal the elongated body, the distal assembly comprising a helical form comprising a proximal loop and a distal loop, and a shape-memory support member extending through at least the proximal loop, the proximal loop having a first flexibility, and the distal loop having a second flexibility that is greater than the first flexibility of the proximal loop, the helical form having a diameter that decreases from a proximal end of the helical form to a distal end of the helical form;
   at least one proximal loop ring electrode mounted on the proximal loop;
   a control handle proximal the elongated body; and
   a contraction wire having a proximal end in the control handle and a distal end anchored in the proximal loop, the control handle including a first control member configured to actuate the contraction wire to contract the proximal loop.

2. The catheter of claim 1, wherein the pitch of the helical form remains constant along a length of the helical form from a proximal end to a distal end of the helical form.

3. The catheter of claim 1, wherein the pitch of the helical form varies along a length of the helical form from a proximal end to a distal end of the helical form.

4. The catheter of claim 3, wherein the pitch of the helical form is greater in the proximal loop and lesser in the distal loop.

5. The catheter of claim 3, wherein the pitch of the helical form is greater in the distal loop and lesser in the proximal loop.

6. The catheter of claim 1, further comprising an angled elbow section at a proximal end of the proximal loop, the angled elbow section having an exposed length of about 4 mm to about 6 mm.

7. The catheter of claim 6, further comprising a transverse curved section at the proximal end of the proximal loop distal of the elbow section, the transverse curved section having an exposed length of about 5 mm to about 7 mm.

8. The catheter of claim 1, wherein the distal loop comprises a generally straight distal end section.

9. The catheter of claim 8, wherein the helical form from a proximal end of the proximal loop to a distal end of the generally straight distal end section has an exposed length of about 18 mm to about 22 mm.

10. The catheter of claim 1, wherein the at least one proximal loop ring electrode comprises an ablation reservoir electrode configured for irrigation and ablation.

11. The catheter of claim 10, wherein the ablation reservoir electrode has a length greater than a diameter of the ablation reservoir electrode.

12. The catheter of claim 11, wherein the ablation reservoir electrode has a length of about 3.0 mm, an outer diameter of about 2.8 mm, and an inner diameter of about 2.33 mm.

13. The catheter of claim 10, wherein the ablation reservoir electrode has a side cross-section resembling a barrel, having a side wall that bulges radially such that a mid portion of the ablation reservoir electrode has a mid portion diameter that is greater than an end portion diameter of both opposing end portions of the ablation reservoir electrode.

14. The catheter of claim 13, wherein the ablation reservoir electrode further comprises a curved transitional region between each opposing end portion and the mid portion to thereby provide an atraumatic profile.

15. The catheter of claim 1, wherein the at least one proximal loop ring electrode comprises a plurality of ablation reservoir electrodes configured for irrigation and ablation, and a plurality of recording ring electrodes configured to record impedance.

16. The catheter of claim 15, wherein at least one of the plurality of recording ring electrodes is located between two adjacent ones of the plurality of ablation reservoir electrodes.

17. The catheter of claim 15, wherein a pair of two of the plurality of recording ring electrodes are located between two adjacent ones of the plurality of ablation reservoir electrodes such that for M plurality of the ablation reservoir electrodes there are 2(M−1) plurality of recording ring electrodes.

18. The catheter of claim 1, wherein the at least one proximal loop ring electrode comprises ten ablation reservoir electrodes configured for irrigation and ablation, the ten ablation reservoir electrodes being spaced from each other on the proximal loop by a distance of about 4.0 mm.

19. The catheter of claim 17, wherein the plurality of ablation reservoir electrodes comprises ten ablation reservoir electrodes with a spacing between adjacent ones of the ablation reservoir electrodes of about 4.0 mm.

20. The catheter of claim 1, wherein the helical form has a diameter of about 20 mm to about 35 mm, and a pitch of about 0.5" to about 0.3".

* * * * *